US012616515B2

(12) United States Patent
Govari

(10) Patent No.: US 12,616,515 B2
(45) Date of Patent: May 5, 2026

(54) ESTIMATION OF ELECTRODE-TISSUE CONTACT USING STEM AND EDGE ELECTRODES

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 910 days.

(21) Appl. No.: 16/553,055

(22) Filed: Aug. 27, 2019

(65) Prior Publication Data

US 2021/0059743 A1    Mar. 4, 2021

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00577* (2013.01); *A61B 2018/00875* (2013.01)

(58) Field of Classification Search
CPC ........ A61B 18/1492; A61B 2018/0022; A61B 2018/00577; A61B 2018/00875
See application file for complete search history.

(56) References Cited

U.S. PATENT DOCUMENTS

| | | |
|---|---|---|
| D123,782 S | 12/1940 | Paul |
| 3,316,896 A | 5/1967 | Louis |

| | | |
|---|---|---|
| 4,276,874 A | 7/1981 | Wolvek et al. |
| 4,587,975 A | 5/1986 | Salo et al. |
| 4,709,698 A | 12/1987 | Johnston et al. |
| 4,805,621 A | 2/1989 | Heinze et al. |
| 5,178,957 A | 1/1993 | Kolpe et al. |
| 5,429,617 A | 7/1995 | Hammersmark et al. |
| 5,582,609 A | 12/1996 | Swanson et al. |

(Continued)

FOREIGN PATENT DOCUMENTS

| | | |
|---|---|---|
| CN | 1895166 A | 1/2007 |
| CN | 101422637 A | 5/2009 |

(Continued)

OTHER PUBLICATIONS

Search Report dated Feb. 29, 2024, from corresponding Japanese Application No. 2020142371A.

(Continued)

*Primary Examiner* — Linda C Dvorak
*Assistant Examiner* — Christine A Dedoulis

(57) ABSTRACT

A system includes an expandable frame and a processor. The expandable frame includes (i) one or more ablation electrodes disposed over an external surface of the frame and configured to be placed in contact with wall tissue of a cavity of a patient, and (ii) stem and edge electrodes coupled just proximally and just distally to the balloon, respectively. The processor is configured to: (a) measure one or more first impedances between one or more of the ablation electrodes and the stem electrode, (b) measure one or more second impedances between one or more of the ablation electrodes and the edge electrode, and (c) based on the first and second impedances, determine, for at least an ablation electrode from among the one or more ablation electrodes, whether the ablation electrode is in physical contact with the wall tissue.

7 Claims, 3 Drawing Sheets

(56)  References Cited

U.S. PATENT DOCUMENTS

| | | | |
|---|---|---|---|
| 5,584,830 A | 12/1996 | Ladd et al. | |
| 5,702,386 A | 12/1997 | Stern et al. | |
| 5,718,241 A | 2/1998 | Ben-Haim et al. | |
| 5,797,903 A | 8/1998 | Swanson et al. | |
| 5,860,974 A | 1/1999 | Abele | |
| 5,971,983 A | 10/1999 | Lesh | |
| 6,012,457 A | 1/2000 | Lesh | |
| 6,024,740 A | 2/2000 | Lesh et al. | |
| 6,042,580 A | 3/2000 | Simpson | |
| 6,123,718 A | 9/2000 | Tu et al. | |
| 6,164,283 A | 12/2000 | Lesh | |
| 6,171,275 B1 | 1/2001 | Webster, Jr. | |
| 6,176,832 B1 | 1/2001 | Habu et al. | |
| 6,198,974 B1 | 3/2001 | Webster, Jr. | |
| 6,226,542 B1 | 5/2001 | Reisfeld | |
| 6,301,496 B1 | 10/2001 | Reisfeld | |
| 6,322,558 B1 | 11/2001 | Taylor et al. | |
| 6,380,957 B1 | 4/2002 | Banning | |
| 6,391,024 B1 | 5/2002 | Sun et al. | |
| 6,402,740 B1 | 6/2002 | Ellis et al. | |
| D462,389 S | 9/2002 | Provence et al. | |
| 6,471,693 B1 | 10/2002 | Carroll et al. | |
| 6,522,930 B1 | 2/2003 | Schaer et al. | |
| 6,656,174 B1 | 12/2003 | Hegde et al. | |
| 6,814,733 B2 | 11/2004 | Schwartz et al. | |
| 6,893,433 B2 | 5/2005 | Lentz | |
| 6,986,744 B1 | 1/2006 | Krivitski | |
| 6,987,995 B2 | 1/2006 | Drysen | |
| 6,997,924 B2 | 2/2006 | Schwartz et al. | |
| 7,142,903 B2 | 11/2006 | Rodriguez et al. | |
| 7,156,816 B2 | 1/2007 | Schwartz et al. | |
| 7,274,957 B2 | 9/2007 | Drysen | |
| 7,340,307 B2 | 3/2008 | Maguire et al. | |
| 7,377,906 B2 | 5/2008 | Selkee | |
| 7,442,190 B2 | 10/2008 | Abbound et al. | |
| 7,536,218 B2 | 5/2009 | Govari et al. | |
| 7,591,799 B2 | 9/2009 | Selkee | |
| 7,593,760 B2 | 9/2009 | Rodriguez et al. | |
| 7,720,517 B2 | 5/2010 | Drysen | |
| 7,756,576 B2 | 7/2010 | Levin | |
| 7,842,031 B2 | 11/2010 | Abboud et al. | |
| 7,848,787 B2 * | 12/2010 | Osadchy | A61B 5/053 |
| | | | 600/373 |
| 7,853,302 B2 | 12/2010 | Rodriguez et al. | |
| 7,869,865 B2 | 1/2011 | Govari et al. | |
| 8,000,765 B2 | 8/2011 | Rodriguez et al. | |
| 8,021,327 B2 | 9/2011 | Selkee | |
| 8,048,032 B2 | 11/2011 | Root et al. | |
| 8,231,617 B2 | 7/2012 | Satake | |
| 8,267,932 B2 | 9/2012 | Baxter et al. | |
| 8,275,440 B2 | 9/2012 | Rodriguez et al. | |
| 8,348,888 B2 | 1/2013 | Selkee | |
| 8,357,152 B2 | 1/2013 | Govari et al. | |
| D682,289 S | 5/2013 | DiJulio et al. | |
| D682,291 S | 5/2013 | Baek et al. | |
| 8,456,182 B2 | 6/2013 | Bar-Tal et al. | |
| D690,318 S | 9/2013 | Kluttz et al. | |
| D694,652 S | 12/2013 | Tompkin | |
| 8,641,709 B2 | 2/2014 | Sauvageau et al. | |
| 8,721,590 B2 | 5/2014 | Seward et al. | |
| 8,777,161 B2 | 7/2014 | Pollock et al. | |
| D716,340 S | 10/2014 | Bresin et al. | |
| 8,852,181 B2 | 10/2014 | Malecki et al. | |
| D720,766 S | 1/2015 | Mandal et al. | |
| D721,379 S | 1/2015 | Moon et al. | |
| D724,618 S | 3/2015 | Shin | |
| 8,998,893 B2 | 4/2015 | Avitall | |
| D729,263 S | 5/2015 | Ahn et al. | |
| 9,089,350 B2 | 7/2015 | Willard | |
| D736,780 S | 8/2015 | Wang | |
| 9,126,023 B1 | 9/2015 | Sahatjian et al. | |
| D740,308 S | 10/2015 | Kim et al. | |
| D743,424 S | 11/2015 | Danielyan et al. | |
| D744,000 S | 11/2015 | Mllamor et al. | |
| 9,173,758 B2 | 11/2015 | Brister et al. | |
| D747,742 S | 1/2016 | Fan et al. | |
| D750,644 S | 3/2016 | Bhutani et al. | |
| 9,283,034 B2 | 3/2016 | Katoh et al. | |
| 9,289,141 B2 | 3/2016 | Lowery et al. | |
| D753,690 S | 4/2016 | Vazquez et al. | |
| 9,320,631 B2 | 4/2016 | Moore et al. | |
| 9,345,540 B2 | 5/2016 | Mallin et al. | |
| D759,673 S | 6/2016 | Looney et al. | |
| D759,675 S | 6/2016 | Looney et al. | |
| D764,500 S | 8/2016 | Wang | |
| D765,709 S | 9/2016 | Gagnier | |
| D767,616 S | 9/2016 | Jones et al. | |
| D768,696 S | 10/2016 | Gagnier | |
| D783,037 S | 4/2017 | Hariharan et al. | |
| 9,655,677 B2 | 5/2017 | Salahieh et al. | |
| D791,805 S | 7/2017 | Segars | |
| 9,795,442 B2 | 10/2017 | Salahieh et al. | |
| 9,907,610 B2 | 3/2018 | Beeckler et al. | |
| 9,956,035 B2 | 5/2018 | Govari et al. | |
| D861,717 S | 10/2019 | Brekke et al. | |
| 10,688,278 B2 | 6/2020 | Beeckler et al. | |
| 2001/0031961 A1 | 10/2001 | Hooven | |
| 2002/0002369 A1 | 1/2002 | Hood | |
| 2002/0065455 A1 | 5/2002 | Ben-Haim et al. | |
| 2002/0068931 A1 | 6/2002 | Wong et al. | |
| 2002/0077627 A1 | 6/2002 | Johnson et al. | |
| 2002/0160134 A1 | 10/2002 | Ogushi et al. | |
| 2003/0018327 A1 | 1/2003 | Truckai et al. | |
| 2003/0028183 A1 | 2/2003 | Sanchez et al. | |
| 2003/0050637 A1 | 3/2003 | Maguire et al. | |
| 2003/0060820 A1 | 3/2003 | Maguire et al. | |
| 2003/0144658 A1 | 7/2003 | Schwartz et al. | |
| 2004/0122445 A1 | 6/2004 | Butler et al. | |
| 2004/0147920 A1 | 7/2004 | Keidar | |
| 2004/0225285 A1 | 11/2004 | Gibson | |
| 2005/0070887 A1 | 3/2005 | Taimisto et al. | |
| 2005/0119686 A1 | 6/2005 | Clubb | |
| 2006/0013595 A1 | 1/2006 | Trezza et al. | |
| 2006/0106375 A1 | 5/2006 | Werneth et al. | |
| 2006/0135953 A1 | 6/2006 | Kania et al. | |
| 2006/0173251 A1 | 8/2006 | Govari et al. | |
| 2007/0060832 A1 | 3/2007 | Levin | |
| 2007/0071792 A1 | 3/2007 | Varner et al. | |
| 2007/0080322 A1 | 4/2007 | Walba | |
| 2007/0083194 A1 | 4/2007 | Kunis et al. | |
| 2007/0255162 A1 * | 11/2007 | Abboud | A61B 5/0537 |
| | | | 600/547 |
| 2007/0287994 A1 | 12/2007 | Patel | |
| 2008/0018891 A1 | 1/2008 | Hell et al. | |
| 2008/0021313 A1 | 1/2008 | Eidenschink et al. | |
| 2008/0051707 A1 | 2/2008 | Phan et al. | |
| 2008/0140072 A1 | 6/2008 | Stangenes et al. | |
| 2008/0183132 A1 | 7/2008 | Davies et al. | |
| 2008/0188912 A1 | 8/2008 | Stone et al. | |
| 2008/0202637 A1 | 8/2008 | Hector et al. | |
| 2008/0208186 A1 | 8/2008 | Slater | |
| 2008/0249463 A1 | 10/2008 | Pappone et al. | |
| 2008/0262489 A1 | 10/2008 | Steinke | |
| 2008/0275465 A1 | 11/2008 | Paul et al. | |
| 2008/0281312 A1 | 11/2008 | Werneth et al. | |
| 2009/0163890 A1 | 6/2009 | Clifford et al. | |
| 2009/0182318 A1 | 7/2009 | Abboud et al. | |
| 2009/0270850 A1 | 10/2009 | Zhou et al. | |
| 2010/0069836 A1 | 3/2010 | Satake | |
| 2010/0079158 A1 | 4/2010 | Bar-Tal et al. | |
| 2010/0114269 A1 | 5/2010 | Wittenberger et al. | |
| 2010/0204560 A1 | 8/2010 | Salahieh et al. | |
| 2010/0256629 A1 | 10/2010 | Wylie et al. | |
| 2010/0324552 A1 | 12/2010 | Kauphusman et al. | |
| 2011/0118632 A1 | 5/2011 | Sinelnikov et al. | |
| 2011/0130648 A1 | 6/2011 | Beeckler et al. | |
| 2011/0282338 A1 | 11/2011 | Fojtik | |
| 2011/0295248 A1 | 12/2011 | Wallace et al. | |
| 2011/0301587 A1 | 12/2011 | Deem et al. | |
| 2011/0313286 A1 | 12/2011 | Whayne et al. | |
| 2012/0019107 A1 | 1/2012 | Gabl et al. | |
| 2012/0029511 A1 | 2/2012 | Smith et al. | |
| 2012/0065503 A1 | 3/2012 | Rogers et al. | |
| 2012/0071870 A1 | 3/2012 | Salahieh et al. | |

(56) References Cited

U.S. PATENT DOCUMENTS

| | | |
|---|---|---|
| 2012/0079427 A1 | 3/2012 | Carmichael et al. |
| 2012/0095461 A1* | 4/2012 | Herscher ............ A61B 18/1492 |
| | | 606/45 |
| 2012/0101413 A1 | 4/2012 | Beetel et al. |
| 2012/0101538 A1 | 4/2012 | Ballakur et al. |
| 2012/0143177 A1 | 6/2012 | Avitall |
| 2012/0143179 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | DeBOER et al. |
| 2014/0243821 A1 | 8/2014 | Salahieh et al. |
| 2014/0275993 A1 | 9/2014 | Ballakur |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2014/0364848 A1 | 12/2014 | Heimbecher et al. |
| 2015/0005799 A1 | 1/2015 | Lindquist et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0141982 A1 | 5/2015 | Lee |
| 2015/0157382 A1 | 6/2015 | Avitall et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2015/0351836 A1* | 12/2015 | Prutchi .............. A61B 18/1492 |
| | | 606/41 |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0256305 A1 | 9/2016 | Longo et al. |
| 2016/0287136 A1 | 10/2016 | Condie |
| 2016/0331459 A1 | 11/2016 | Townley et al. |
| 2016/0374748 A9 | 12/2016 | Salahieh et al. |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0086748 A1 | 3/2017 | Ghaffari et al. |

| | | |
|---|---|---|
| 2017/0143359 A1 | 5/2017 | Nguyen et al. |
| 2017/0164464 A1 | 6/2017 | Weinkam et al. |
| 2017/0164999 A1 | 6/2017 | Hettel |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2018/0074693 A1 | 3/2018 | Jones et al. |
| 2018/0110562 A1 | 4/2018 | Govari et al. |
| 2018/0125575 A1 | 5/2018 | Schwartz et al. |
| 2018/0256247 A1 | 9/2018 | Govari et al. |
| 2018/0280080 A1 | 10/2018 | Govari et al. |
| 2018/0333162 A1 | 11/2018 | Saab |
| 2018/0368927 A1 | 12/2018 | Lyons et al. |
| 2019/0030328 A1 | 1/2019 | Stewart et al. |
| 2019/0059818 A1 | 2/2019 | Herrera et al. |
| 2019/0060622 A1 | 2/2019 | Beeckler |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0297441 A1 | 9/2019 | Dehe et al. |
| 2019/0298441 A1 | 10/2019 | Clark et al. |
| 2019/0365451 A1 | 12/2019 | Jung, Jr. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0155226 A1 | 5/2020 | Valls et al. |
| 2020/0179029 A1 | 6/2020 | Coulombe et al. |
| 2021/0169567 A1 | 6/2021 | Govari et al. |

FOREIGN PATENT DOCUMENTS

| | | |
|---|---|---|
| CN | 102271607 A | 12/2011 |
| CN | 102458566 A | 5/2012 |
| CN | 103068330 A | 4/2013 |
| CN | 103190951 A | 7/2013 |
| CN | 203539434 U | 4/2014 |
| CN | 104244856 A | 12/2014 |
| CN | 104546117 A | 4/2015 |
| CN | 104837430 A | 8/2015 |
| CN | 105105844 A | 12/2015 |
| CN | 105473091 A | 4/2016 |
| CN | 105473093 A | 4/2016 |
| CN | 105873536 A | 8/2016 |
| EP | 0779059 A1 | 6/1997 |
| EP | 1790304 A2 | 5/2007 |
| EP | 2749214 A1 | 7/2014 |
| EP | 2865350 A2 | 4/2015 |
| EP | 2875790 A2 | 5/2015 |
| EP | 3238646 A2 | 11/2017 |
| EP | 3238648 A1 | 11/2017 |
| EP | 3251622 A1 | 12/2017 |
| EP | 3300680 A1 | 4/2018 |
| EP | 3315087 A1 | 5/2018 |
| EP | 3332727 A2 | 6/2018 |
| EP | 3571983 A2 | 11/2019 |
| EP | 3586778 A1 | 1/2020 |
| EP | 3653153 A1 | 5/2020 |
| JP | H06261951 A | 9/1994 |
| JP | H1176233 A | 3/1999 |
| JP | 2000504242 A | 4/2000 |
| JP | 2005052424 A | 3/2005 |
| JP | 2010507404 A | 3/2010 |
| JP | 2012024156 A | 2/2012 |
| JP | 2013013726 A | 1/2013 |
| JP | 2013078587 A | 5/2013 |
| JP | 2013529109 A | 7/2013 |
| JP | 2014529419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016515442 A | 5/2016 |
| JP | 2016116863 A | 6/2016 |

(56) References Cited

FOREIGN PATENT DOCUMENTS

| JP | 2016147018 A | 8/2016 |
|----|--------------|--------|
| JP | 2016524480 A | 8/2016 |
| JP | 2018535739 A | 12/2018 |
| WO | 0056237 A2 | 9/2000 |
| WO | 02102231 A2 | 12/2002 |
| WO | 2005041748 A2 | 5/2005 |
| WO | 2008049087 A2 | 4/2008 |
| WO | 2011143468 A2 | 11/2011 |
| WO | 2013049601 A2 | 4/2013 |
| WO | 2013052919 A2 | 4/2013 |
| WO | 2013154776 A2 | 10/2013 |
| WO | 2014168987 A1 | 10/2014 |
| WO | 2015049784 A1 | 4/2015 |
| WO | 2016183337 A2 | 11/2016 |
| WO | 2016210437 A1 | 12/2016 |
| WO | 2017024306 A1 | 2/2017 |
| WO | 2017087549 A1 | 5/2017 |
| WO | 2018106569 A1 | 6/2018 |
| WO | 2018129133 A1 | 7/2018 |
| WO | 2019095020 A1 | 5/2019 |

OTHER PUBLICATIONS

Notice of Reasons for Refusal with English translation dated Mar. 5, 2024, from corresponding Japanese Application No. 2020142371A.

Written Opinion with English translation dated May 21, 2024, from corresponding Japanese Application No. 2020142371A.

Decision to Grant a Patent with English translation dated Jul. 2, 2024, from corresponding Japanese Application No. 2020142371A.

First Search Report dated Nov. 12, 2024, from corresponding Chinese Application No. 202010876979.4.

First Office Action dated Nov. 12, 2024, from corresponding Chinese Application No. 202010876979.4.

Supplemental Search dated Mar. 31, 2025, from corresponding Chinese Application No. 202010876979.4.

Second Office Action dated May 31, 2025, from corresponding Chinese Application No. 202010876979.4.

Extended European Search Report and Opinion dated Jan. 21, 2021, from corresponding European Application No. 20192795.1.

English translation of Search Report dated Feb. 29, 2024, from corresponding Japanese Application No. JP2020-142371.

English translation Notice of Reasons for Refusal dated Mar. 5, 2024, from corresponding Japanese Application No. JP2020-142371.

English translation of Decision to Grant Patent dated Jul. 2, 2024, from corresponding Japanese Application No. JP2020-142371.

Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.

Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.

Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.

Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.

Extended European Search Report for Application No. EP17168513.4 mailed Sep. 18, 2017, 11 pages.

Extended European Search Report for European Application No. 15201723.2, mailed May 11, 2016, 07 Pages.

Extended European Search Report for European Application No. 17168393.1 mailed Dec. 15, 2017, 12 Pages.

Extended European Search Report for European Application No. 17168518.3, mailed Sep. 20, 2017, 9 Pages.

Extended European Search Report for European Application No. 17173893.3, mailed Nov. 6, 2017, 8 Pages.

Extended European Search Report for European Application No. 17201434.2, mailed Feb. 1, 2018, 10 Pages.

Extended European Search Report for European Application No. 17205876.0, mailed Jun. 1, 2018, 13 Pages.

Extended European Search Report for European Application No. 19177365.4, mailed Nov. 8, 2019, 07 Pages.

Extended European Search Report for European Application No. 19183327.6, mailed Nov. 21, 2019, 8 Pages.

Extended European Search Report for European Application No. 20153872.5, mailed May 7, 2020, 9 Pages.

Extended European Search Report for European Application No. 20195648.9, mailed Feb. 12, 2021, 8 Pages.

Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.

Haines D.E., et al., "The Promise of Pulsed Field Ablation," Dec. 2019, vol. 19, No. 12, 10 pages.

Honarbakhsh S., et al., "Radiofrequency Balloon Catheter Ablation for Paroxysmal Atrial Fibrillation, Radiance Study-a UK experience," EP Europace, Oct. 2017, vol. 19, No. 1, p. 121, 3 p.

International Search Report and Written Opinion for International Application No. PCT/IB2019/052313, mailed Jul. 22, 2019, 8 Pages.

International Search Report and Written Opinion for International Application No. PCT/IB2019/056381, mailed Dec. 17, 2019, 10 pages.

International Search Report and Written Opinion for International Application No. PCT/IB2019/057743, mailed Dec. 6, 2019, 16 Pages.

International Search Report and Written Opinion issued in corresponding International Application No. PCT/IB2019/057742, dated Nov. 28, 2019, 18 Pages.

Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.

Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.

Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.

Partial European Search Report for European Application No. 17168393.1 mailed Sep. 13, 2017, 13 Pages.

Partial European Search Report for European Application No. 17205876.0, mailed Feb. 22, 2018, 10 Pages.

Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 p.

Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.

Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QKMWJME].

(56) References Cited

OTHER PUBLICATIONS

Youtube: "New Interface TactiCath Contact Force Ablation Catheter," Nov. 26, 2013, 1 Pages, [Retrieved on Nov. 19, 2020], Retrieved from URL: https: /Avww.youtube.com/watch?v= aYvYO8Hpylg].

"Medical Instrumentation: Application and Design," Webster (ed.) 3rd Ed., John Wiley & Sons, Inc., New York, 1998, pp. 34-53.

\* cited by examiner

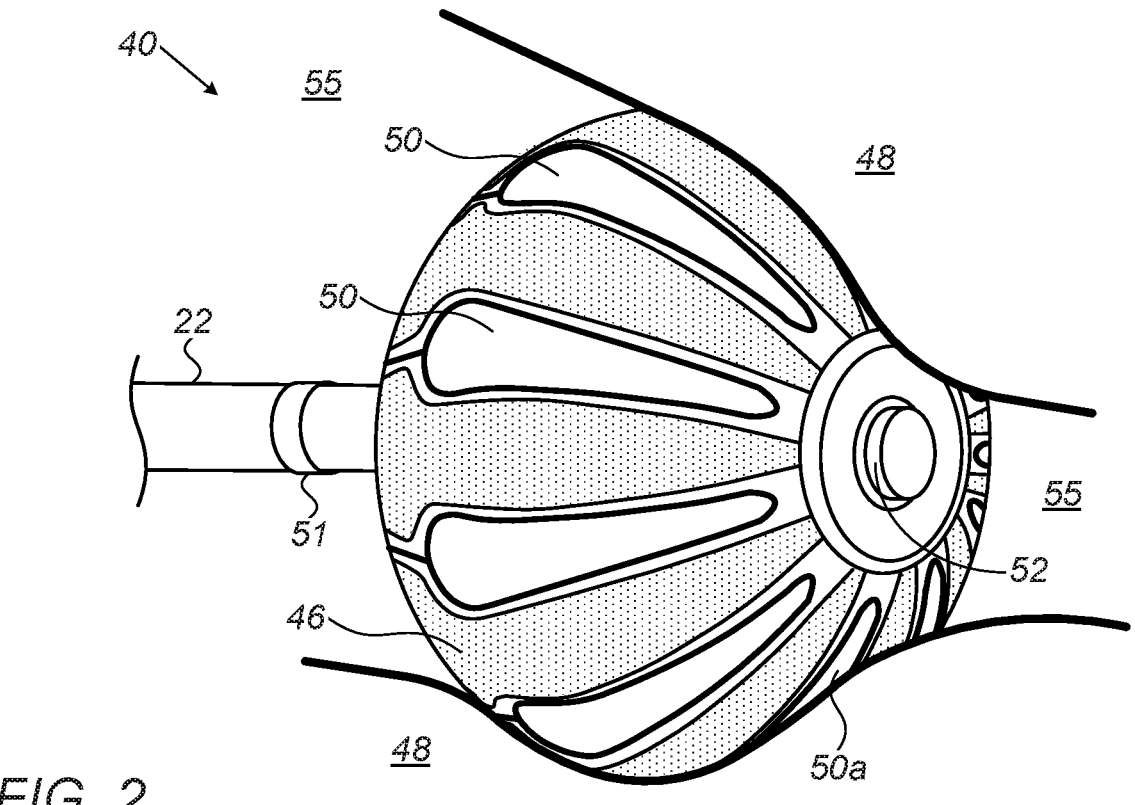
*FIG. 2*
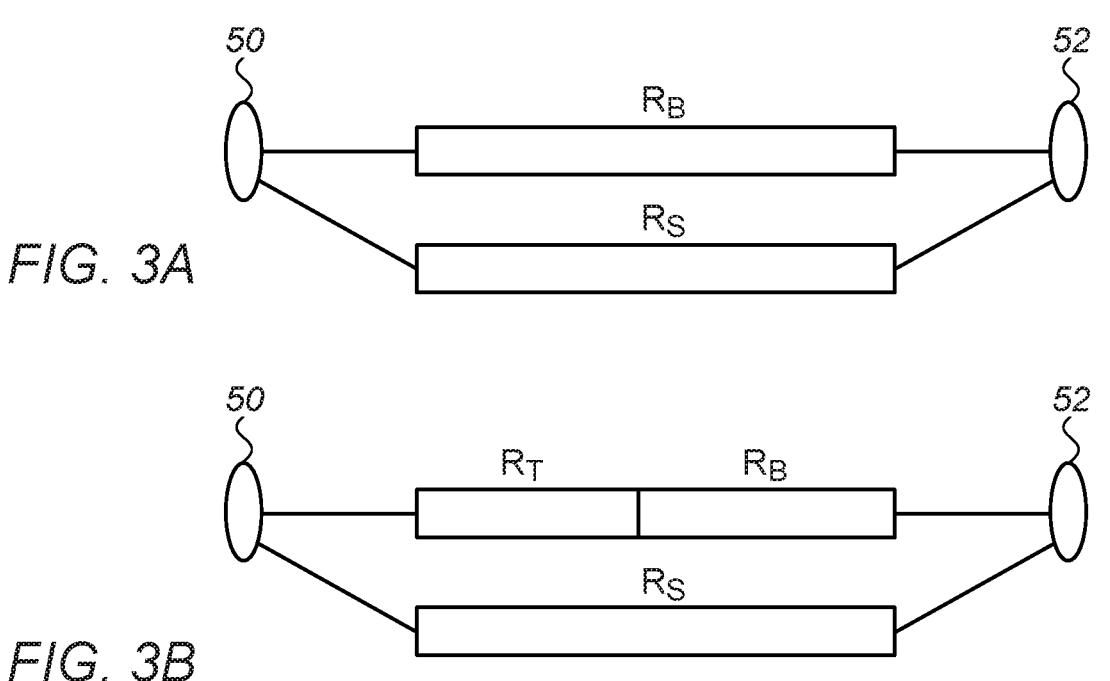
*FIG. 3A*
*FIG. 3B*

ESTIMATION OF ELECTRODE-TISSUE CONTACT USING STEM AND EDGE ELECTRODES

FIELD OF THE INVENTION

The present invention relates generally to medical probes, and particularly to multi-electrode cardiac ablation catheters.

BACKGROUND OF THE INVENTION

Various techniques for verifying contact of an electrode of a catheter with cardiac tissue have been proposed in the patent literature. For example, U.S. Patent Application Publication 2007/0255162 describes methods and systems for providing tissue contact assessment, by providing a catheter having a shaft having a plurality of electrodes, positioning the catheter at a tissue treatment site, applying an electrical current between at least two of the plurality of electrodes, measuring impedance voltage between the at least two of the plurality of electrodes and, processing the measured impedance voltage caused by the applied electrical current to provide contact assessment.

As another example, U.S. Patent Application Publication 2012/0143179 describes a plurality of catheter-based ablation apparatus embodiments, including balloon catheters, that address several areas of atrial target tissue and which feature firm and consistent ablation element to tissue contact, to enable the creation of effective continuous lesions. In an embodiment, energy may be applied to a distal ring electrode of a balloon catheter, together with a reference electrode positioned on the balloon catheter shaft just proximal to the balloon, to measure the conductance across the balloon. If the balloon solidly occludes the PV, the impedance rises and the measurement can also be used to verify PV occlusion.

SUMMARY OF THE INVENTION

An embodiment of the present invention provides a system including an expandable frame and a processor. The expandable frame is coupled to a distal end of a shaft for insertion into a cavity of an organ of a patient and includes one or more ablation electrodes disposed over an external surface of the frame, wherein the one or more ablation electrodes are configured to be placed in contact with wall tissue of the cavity. The expandable balloon further includes a stem electrode coupled to the distal end of the shaft proximally to the balloon, and an edge electrode coupled to the distal end of the shaft distally to the balloon. The processor is configured to: (a) measure one or more first impedances between one or more of the ablation electrodes and the stem electrode, (b) measure one or more second impedances between one or more of the ablation electrodes and the edge electrode, and (c) based on the first and second impedances, determine, for at least an ablation electrode from among the one or more ablation electrodes, whether the ablation electrode is in physical contact with the wall tissue.

In some embodiments, the processor is configured to determine that the ablation electrode is in physical contact with the tissue by determining that a measured first or second impedance is larger than a prespecified impedance by at least a prespecified minimal value.

In some embodiments, the prespecified impedance is measured with the ablation electrode being in contact with blood.

In an embodiment, the prespecified minimal value is stored in a look-up table.

In another embodiment, the system further includes a relay that is configured to switch, under control of the processor, between two or more of: (i) a first configuration for measuring impedances between the ablation electrodes and the stem and edge electrodes, (ii) a second configuration for measuring impedances between the ablation electrodes and one or more body-surface electrodes, and (iii) a third configuration for performing ablation by driving an electrical signal between the ablation electrodes and a back patch electrode.

In some embodiments, the expandable frame includes an expandable balloon and the external surface of the frame includes an external surface of a membrane of the balloon.

There is additionally provided, in accordance with an embodiment of the present invention, a method including inserting into a cavity of an organ of a patient an expandable balloon coupled to a distal end of a shaft, the expandable balloon including one or more ablation electrodes disposed over an external surface of a membrane of the balloon, a stem electrode coupled to the distal end of the shaft proximally to the balloon, and an edge electrode coupled to the distal end of the shaft distally to the balloon. One or more of the ablation electrodes are placed in contact with wall tissue of the cavity. One or more first impedances between one or more of the ablation electrodes and the stem electrode are measured. One or more second impedances between one or more of the ablation electrodes and the edge electrode are measured. Based on the first and second impedances, it is determined, for at least an ablation electrode from among the one or more ablation electrodes, whether the ablation electrode is in physical contact with the wall tissue.

The present invention will be more fully understood from the following detailed description of the embodiments thereof, taken together with the drawings in which:

BRIEF DESCRIPTION OF THE DRAWINGS

FIG. 2 is a schematic pictorial illustration of the balloon catheter of FIG. 1 in physical contact with cavity wall tissue, in accordance with an embodiment of the present invention;

FIGS. 3A and 3B are schematic electrical diagrams of an ablation electrode coupled to an edge electrode while the ablation electrode is in partial contact and in full contact with tissue, respectively, in accordance with an embodiment of the present invention.

DETAILED DESCRIPTION OF EMBODIMENTS

Overview

Figure 1:
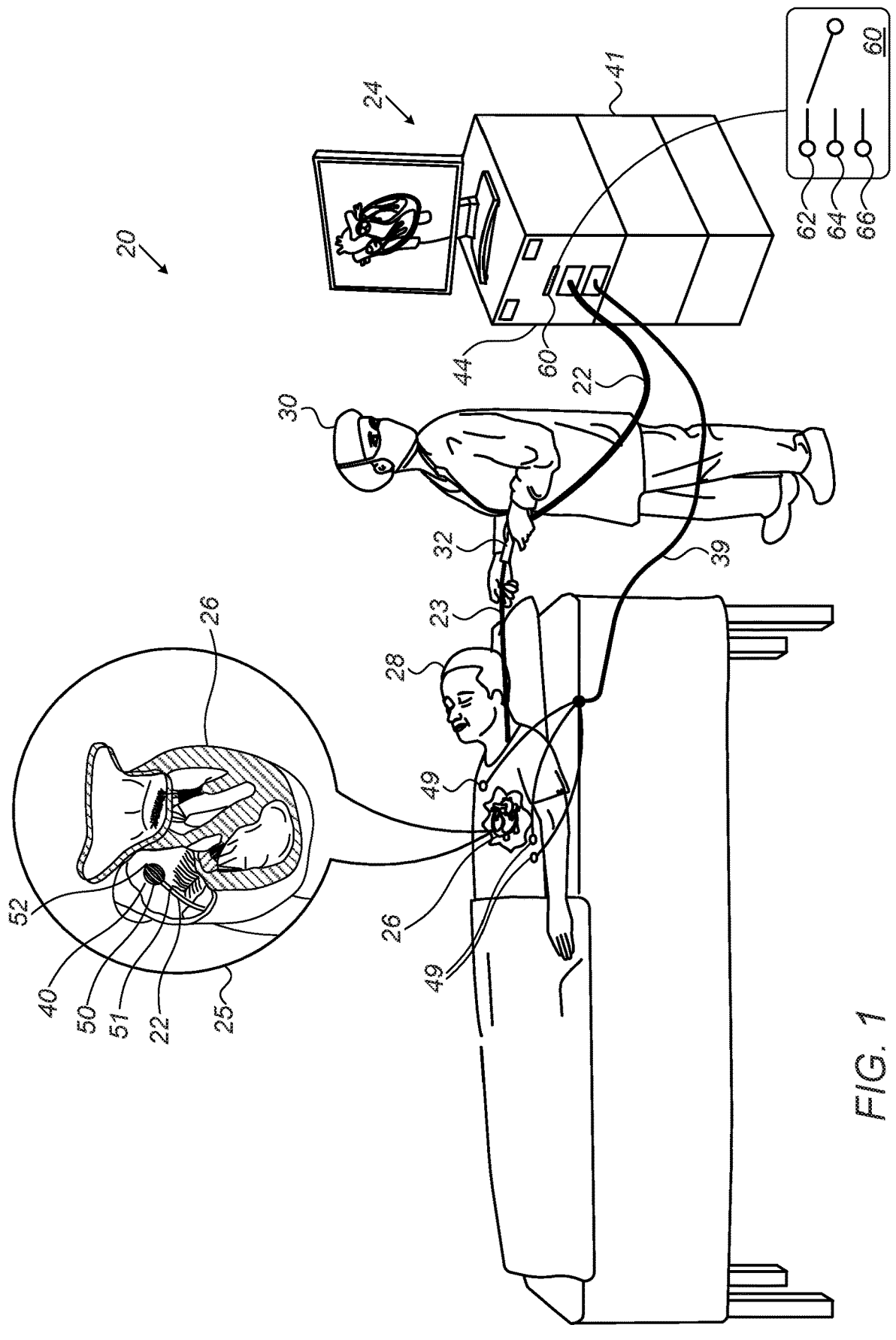
FIG. 1 is a schematic pictorial illustration of a catheter-based position-tracking and ablation system comprising an ablation expandable catheter in the form of a balloon, in accordance with an embodiment of the present invention.

A multi-electrode ablation catheter, such as a balloon ablation catheter or a basket catheter, typically comprises an expandable frame (e.g., an inflatable balloon) that is coupled to the distal end of a shaft for insertion into a cavity of an organ of a patient. For the best outcome of ablation treatment, a physician may need to determine that each of the ablating electrodes disposed over the frame (e.g., balloon) is in physical contact with cavity wall tissue to be ablated. For example, when a balloon catheter with multiple ablation electrodes is used to ablate an ostium of a pulmonary ventricle (PV), typically all of the ablation electrodes of the catheter should be positioned so they are in full contact with the PV tissue.

Many times, however, some of the ablation electrodes may not be in full contact with tissue, but, instead, different portions of some of the ablation electrodes are immersed in blood. For these electrodes, rather than ablating tissue, the applied electrical power may cause unwanted side effects such as clot formation.

Embodiments of the present invention that are described hereinafter provide a system and methods capable of determining if an ablation electrode is in full contact with tissue (e.g., being entirely covered by tissue). In some embodiments, a balloon ablation catheter is provided that comprises (i) at least one ablation electrode, (ii) an electrode disposed on the distal end of the shaft just proximally to the balloon (named hereinafter "stem electrode"), and (iii) an electrode disposed on the distal end of the shaft just distally to the balloon (named hereinafter "edge electrode"). Using impedance measurements between each ablation electrode and the stem and edge electrodes, a processor of the ablation system determines, for each ablation electrode, if the ablation electrode is in full contact with tissue.

In some embodiments, the processor of the system compares measured in-situ impedances between an ablation electrode intended to have contact with tissue, and the stem and edge electrodes when the ablation electrode is at least partially exposed to blood, to the same measured impedances. In the case of full contact, the impedances measured in-situ should be larger than the impedances measured with an ablation electrode in blood by at least a prespecified minimal value. Depending on, for example, the number of electrodes already in full contact with tissue, different minimal values of impedance-difference may be prespecified. The prespecified minimal values can be stored, for example, in a look-up table.

The above-mentioned prespecified minimal impedance-difference values are determined at a typical RF frequency of a few kHz, at which cardiac tissue impedance is typically several times higher than that of blood (in some cases, approximately 300Ω in tissue vs. approximately 100Ω in blood). Further information on tissue vs blood impedances as a function of RF frequencies is available, for example, in "Medical Instrumentation: Application and Design," Webster (ed.) 3rd Ed., John Wiley & Sons, Inc., New-York, 1998.

The disclosed measurement geometry involves comparable path lengths in blood and tissue, so the measured impedances mainly change due to different tissue properties. This characteristic of the disclosed technique gives a high degree of certainty to the distinction made by the processor based on the measurements between blood contact and tissue contact.

In order to verify that full physical contact with tissue has been achieved from both ends of the elongated ablation electrodes (i.e., proximal and distal), it is required to perform the measurements relative to the stem and edge electrodes.

If full physical contact is not achieved for all ablation electrodes, the physician may maneuver the balloon catheter to establish more complete contact of the ablation electrodes with tissue, and again check the sufficiency of contact using the disclosed technique.

In some embodiments, in order to measure a balloon catheter position inside the organ, the ablation system includes a position tracking sub-system that measures impedances between the ablation electrodes and surface electrodes. The method, which is further described below, is sometimes called Advanced Catheter Location (ACL). Using a relay, the system can switch electrical connections between the ablation electrodes and surface electrodes and between the ablation electrodes the stem and edge electrodes of the balloon catheter in order to interchangeably measure electrode position and degree of electrode contact with tissue at the location.

Furthermore, using the relay, the system can switch electrical connections between the ablation electrodes and either the stem and edge electrodes (for assessing contact) or the surface electrodes (for measuring positions) to a back patch electrode, for performing ablation by driving electrical signal between the ablation electrodes and the back patch electrode.

Typically, the processor is programmed in software containing a particular algorithm that enables the processor to conduct each of the processor-related steps and functions outlined hereinafter.

By determining, in real-time, which ablation electrode is in full contact with tissue and which is not, the disclosed technique may increase the safety and effectiveness of multi-electrode ablation treatments.

System Description

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment. FIG. 1 is a schematic pictorial illustration of a catheter-based position-tracking and ablation system comprising an ablation balloon catheter 40, in accordance with an embodiment of the present invention. Typically, balloon catheter 40 is used for therapeutic treatment, such as ablating cardiac tissue, for example at the left atrium. System 20 is used to determine the position of balloon catheter 40, seen in an inset 25 coupled to a distal end of a shaft 22. System 20 is further used to determine, e.g., prior to performing an ablation, whether each of ablation electrodes 50 of balloon catheter 40 is in contact with tissue.

Physician 30 navigates balloon catheter 40 to a target location in a heart 26 of a patient 28 by manipulating shaft 22 using a manipulator 32 near the proximal end of the catheter and/or deflection from a sheath 23. Balloon catheter 40 is inserted, in a folded configuration, through sheath 23, and only after the balloon is retracted from the sheath 23 does balloon catheter 40 regain its intended functional shape. By containing balloon catheter 40 in a folded configuration, sheath 23 also serves to minimize vascular trauma on its way to the target location.

Balloon catheter 40 comprises elongated and large area ablation electrodes 50, which are disposed on an outer surface of the balloon membrane. A stem electrode 51 is disposed on a distal end of shaft 22 just proximally to the balloon. An edge electrode 52 is disposed on the distal end of shaft 22 just distally to the balloon. Electrodes 51 and 52 are used to determine whether each of ablation electrodes 50 is in full contact with tissue or at least partially immersed in blood.

Ablation electrodes 50, stem electrode 51, and edge electrode 52 are connected by wires running through shaft 22 to interface circuits 44 in a console 24. A detailed view of balloon catheter 40 with ablation electrodes 50, stem electrode 51, and edge electrode 52 is shown in FIG. 2.

Additionally, using the aforementioned ACL method, ablation electrodes 50 can be used to measure a position of balloon catheter 40 inside heart 26, by sensing impedances relative to surface electrodes 49, which are seen in the exemplified system as attached by wires running through a cable 39 to the chest of patient 28. The ACL method for tracking the positions of electrodes 50 is implemented in various medical applications, for example in the CARTO™ system, produced by Biosense-Webster Inc. (Irvine, California) and is described in detail in U.S. Pat. Nos. 7,756,576, 7,869,865, 7,848,787, and 8,456,182, whose disclosures are all incorporated herein by reference. Console 24 drives a display 27, which shows the tracked position of balloon catheter 40 inside heart 26.

Console 24 comprises a processor 41, typically a general-purpose computer and a suitable front end and interface circuits 44 for transmitting and receiving signals, such as RF signals and position signals, respectively. Interface circuits 44 may also receive electrocardiograms from surface electrodes 49 and/or from any electrode disposed on the catheter.

In some embodiments, processor 41 controls a relay 60 in system 20 to switch electrical connections between two or more of: (i) a first configuration having a connection (62) between the ablation electrodes and surface electrodes 49 for measuring impedances between the ablation electrodes and one or more body-surface electrodes, (ii) a second configuration having a connection (64) between the ablation electrodes and the stem and edge electrodes of the balloon catheter for measuring impedances between the ablation electrodes and the stem and edge electrodes, where connections 62 and 64 are used in order to interchangeably measure electrode position and degree of electrode contact with tissue at the location, and (iii) a connection (66) between the ablation electrodes and a back patch electrode (not shown) in order to perform ablation by driving electrical signal between the ablation electrodes and the back patch electrode.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, including in FIG. 4, that enables processor 41 to perform the disclosed steps, as further described below.

FIG. 1 shows only elements related to the disclosed techniques, for the sake of simplicity and clarity. System 20 typically comprises additional modules and elements that are not directly related to the disclosed techniques, such as irrigation and temperature modules, and thus are intentionally omitted from FIG. 1 and from the corresponding description.

Estimation of Balloon Electrode-Tissue Contact Using Stem and Edge Electrodes FIG. 2 is a schematic pictorial illustration of balloon catheter 40 of FIG. 1 in physical contact with cavity wall tissue 48, in accordance with an embodiment of the present invention. Balloon catheter 40 comprises ablation electrodes 50 that are disposed over a membrane 46 of the balloon. Stem electrode 51 and edge electrode 52 are disposed on the distal end of shaft 22 and are immersed in blood 55.

As seen, an ablation electrode 50 at the top of the balloon is in full contact with tissue, i.e., over an entire area of the electrode. An electrode 50 at the bottom, on the other hand, has a distal area 50a that is immersed in blood 55. Correspondingly, different measured impedance values between the top and bottom ablation electrodes and edge electrode 52, which are indicative of the full and partial contact of the top and bottom ablation electrodes with tissue, respectively, are described in FIG. 3.

FIG. 2 is brought by way of example, and is simplified for clarity of presentation. For example, balloon elements not relevant to the embodied invention, such as temperature sensors and irrigation holes, are omitted for simplicity.

FIGS. 3A and 3B are schematic electrical diagrams of an ablation electrode 50 coupled to an edge electrode 52 while ablation electrode 50 is in partial contact and in full contact with tissue 48, respectively, in accordance with an embodiment of the present invention. The diagram of FIG. 3A describes a case of ablation electrode 50 having a distal area, such as area 50a seen in FIG. 2, that is immersed in blood 55, resulting in electrode 50 having insufficient tissue contact. As seen, the impedance between ablation electrode 50 and edge electrode 52 equals that of blood, $R_B$, in parallel to a shunt resistance $R_S$ that might result from blood and/or tissue and/or other electrically conductive intra-body channel. In brief notation this is represented as $|Z\_insufficient|=R_B\|R_S$. A minimal value of Z_insufficient is about $R_B/2$, in case that a balloon mostly immersed in blood so that the shunt resistivity is dominated by blood resistivity. A maximal value is $R_B$ in case of infinite shunt resistivity. For typical blood resistivity value of approximately 100 Ohms, Z_insufficient falls in the range of 50-100 Ohms.

The diagram of FIG. 3B describes the case of an ablation electrode 50 that is completely in contact (i.e., covered in its entirety) by tissue. As seen, the impedance between ablation electrode 50 and edge electrode 52 is of blood in series with tissue, $R_B+R_T$, in parallel to the shunt resistance $R_S$. In brief notation this is represented as $|Z\_sufficient|=(R_B+R_T)\|R_S$. As tissue impedance is considerably larger than that of blood, as described above, a "sufficient" impedance can typically be larger than an "insufficient" impedance by a value large enough to be measured, e.g., at least several ohms, and thus the disclosed method can differentiate between the two cases, using, for example, a calibrated threshold impedance value.

A minimal value of Z_sufficient is about $R_B$, in case that a balloon mostly immersed in blood so that the shunt resistivity is dominated by blood resistivity, in which case repositioning of the balloon is required due to low shunt resistivity. A practical threshold value for Z_sufficient is $R_T$ in case of a shunt resistivity is mainly via tissue. For typical blood resistivity value of approximately 100 Ohms and tissue resistivity value of 300 Ohams, Z_sufficient falls above 150 Ohms. Yet, lower number, which is still above approximately 100 ohms, can be used as a threshold for Z_sufficient, depending, for example, on measurement repeatability.

In an embodiment, processor 41 is configured to determine that the ablation electrode is in physical contact with the tissue by determining that a measured first or second impedance is larger than a prespecified impedance by at least a prespecified minimal value given in a look-up table having, by way of example the form of Table I:

TABLE I

| Level of Contact | prespecified minimal value |
| --- | --- |
| Minimally sufficient | About 110 Ohms |
| Sufficient | About 130 Ohms |
| Good | About 150 Ohms |
| Excellent | About 200 Ohms |

FIGS. 3A and 3B are fully applicable to stem electrode 51. By measuring the impedance between ablation electrodes 50 and both stem electrode 51 and edge electrode 52, the disclosed technique verifies that full physical contact with tissue has been achieved from both ends of the elongated ablation electrodes.

The electrical diagrams shown in FIGS. 3A and 3B are highly simplified, with the aim of presenting the concept. Actual values may be determined empirically or by a more elaborate electrical model.

Figure 4:
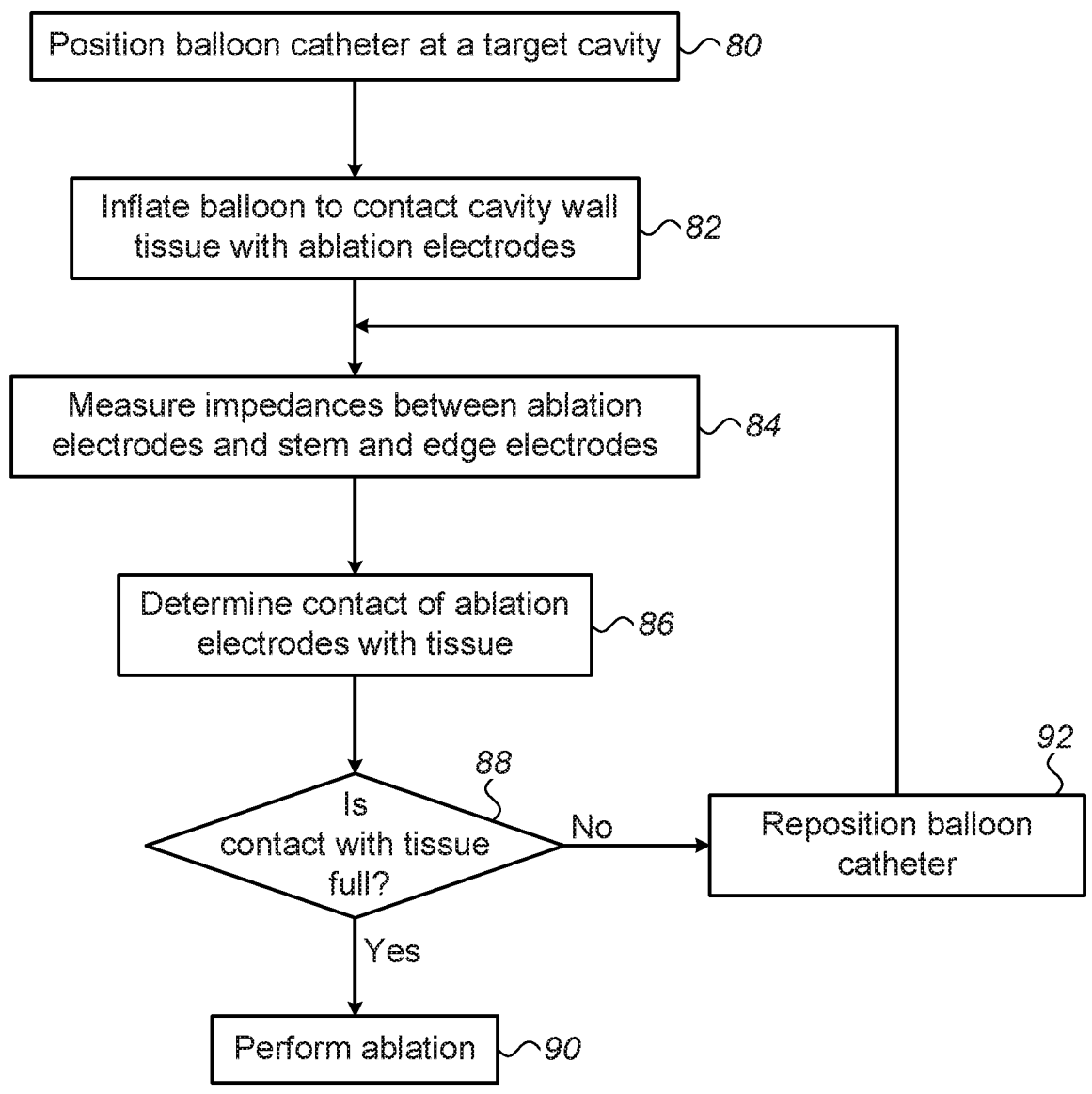
FIG. 4 is a flow chart that schematically illustrates a method and algorithm for determining ablation electrode full contact with tissue, in accordance with an embodiment of the present invention.

FIG. 4 is a flow chart that schematically illustrates a method and algorithm for determining full contact of ablation electrode with tissue, in accordance with an embodiment of the present invention. The algorithm according to the present embodiment carries out a process that begins with physician 30 positioning a partially expanded balloon catheter 40 at a target location inside a cardiac cavity of heart 26, such as at an ostium of a pulmonary vein, at a balloon positioning step 80. Next, physician 30 expands the balloon to bring ablation electrode 50 into full contact with tissue, in a balloon expansion step 82. Next, at a impedances measurement step 74, system 20 measures impedances between each of ablation electrodes 50 and stem (51) and edge (52) electrodes.

At a physical contact determination step 86, based on the measured impedances, processor 41 determines, for each ablation electrode 50, whether the electrode is in full contact with tissue, as defined above. If, at a contact checking step 88, the processor determines that all ablation electrodes 50 are in full contact with tissue, the process continues to perform ablation, at an ablation step 90. If, on the other hand, one or more electrodes are determined by processor 41 to have insufficient contact with tissue (due to insufficient impedance (Table I) as measured by the electrode(s)), physician 30 then repositions balloon catheter 40 in an attempt to improve contact, and the process loops back to step 84, to reassess sufficiency of contact.

The example flow chart shown in FIG. 4 is chosen purely for the sake of conceptual clarity. The present embodiment also comprises additional steps of the algorithm, such as acquiring intra-cardiac electrocardiograms, which have been omitted from the disclosure herein purposely on order to provide a more simplified flow chart. In addition, other steps, such as temperature measurements and applying irrigation, are omitted for clarity of presentation.

Although the embodiments described herein mainly address cardiac applications, the methods and systems described herein can also be used in other applications, such as in renal denervation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur in persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:

an expandable frame coupled to a distal end of a shaft for insertion into a cavity of an organ of a patient, the expandable frame comprising one or more ablation electrodes disposed over an external surface of the frame, wherein the one or more ablation electrodes are configured to be placed in contact with wall tissue of the cavity;

a stem electrode coupled to the distal end of the shaft proximally to the expandable frame, and an edge electrode coupled to the distal end of the shaft distally to the expandable frame; and a processor, which is configured to:

measure one or more first impedances between one or more of the ablation electrodes and the stem electrode;

measure one or more second impedances between one or more of the ablation electrodes and the edge electrode; and determine, for at least one ablation electrode from among the one or more ablation electrodes, based on the one or more first impedances and the one or more second impedances, whether said at least one ablation electrode is in physical contact with the wall tissue.

2. The system according to claim 1, wherein the processor is configured to determine that the ablation electrode is in physical contact with the tissue by determining that a measured first or second impedance is larger than a prespecified impedance by at least a prespecified minimal value.

3. The system according to claim 2, wherein the prespecified impedance is measured with the ablation electrode being in contact with blood.

4. The system according to claim 2, wherein the prespecified minimal value is stored in a look-up table.

5. The system according to claim 1, wherein the expandable frame comprises an expandable balloon and wherein the external surface of the frame comprises an external surface of a membrane of the balloon.

6. The system according to claim 4, wherein the prespecified impedance comprises approximately 100 to approximately 130 ohms as measured by the electrode.

7. The system according to claim 1, and comprising a relay that is configured to switch, under control of the processor, between two or more of: (i) a first configuration for measuring impedances between the ablation electrodes and the stem and edge electrodes, (ii) a second configuration for measuring impedances between the ablation electrodes and one or more body-surface electrodes, and (iii) a third configuration for performing ablation by driving an electrical signal between the ablation electrodes and a back patch electrode.

* * * * *